(12) United States Patent
Semoff

(10) Patent No.: US 10,415,178 B1
(45) Date of Patent: *Sep. 17, 2019

(54) NON-WOVEN FABRIC SHEET

(71) Applicant: Scent2Market Inc., Yonkers, NY (US)

(72) Inventor: Steven Semoff, New York, NY (US)

(73) Assignee: Scent2Market, Inc., Yonkers, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/432,192

(22) Filed: Jun. 5, 2019

Related U.S. Application Data

(63) Continuation of application No. 16/240,023, filed on Jan. 4, 2019, now Pat. No. 10,358,766, which is a continuation-in-part of application No. 16/020,075, filed on Jun. 27, 2018, which is a continuation of application No. 29/631,240, filed on Dec. 28, 2017.

(60) Provisional application No. 62/635,324, filed on Feb. 26, 2018.

(51) Int. Cl.
| | |
|---|---|
| *A61L 9/012* | (2006.01) |
| *D06M 11/83* | (2006.01) |
| *D06M 15/263* | (2006.01) |
| *D06M 17/04* | (2006.01) |
| *D06M 101/32* | (2006.01) |
| *D06M 101/06* | (2006.01) |

(52) U.S. Cl.
CPC ............ *D06M 11/83* (2013.01); *A61L 9/012* (2013.01); *D06M 15/263* (2013.01); *D06M 17/04* (2013.01); *A61L 2209/13* (2013.01); *D06M 2101/06* (2013.01); *D06M 2101/32* (2013.01); *D06M 2200/00* (2013.01)

(58) Field of Classification Search
None
See application file for complete search history.

(56) References Cited

U.S. PATENT DOCUMENTS

| | | |
|---|---|---|
| D441,539 S | 5/2001 | Streit |
| 7,794,737 B2 | 9/2010 | Fish et al. |
| D681,110 S | 4/2013 | Sato et al. |
| 9,233,516 B2 | 1/2016 | Kusin et al. |
| 9,795,142 B2 | 10/2017 | Hitchcock et al. |
| 9,949,609 B2 | 4/2018 | Baer et al. |
| 2011/0156381 A1 | 6/2011 | Kuo et al. |
| 2012/0123380 A1 | 5/2012 | Deerin |
| 2016/0274461 A1* | 9/2016 | Brust ............... G03F 7/0388 |

* cited by examiner

*Primary Examiner* — Robert A Wax
*Assistant Examiner* — Melissa S Mercier
(74) *Attorney, Agent, or Firm* — Buchanan Ingersoll & Rooney PC

(57) ABSTRACT

Disclosed is a malodor control system that can include use of a malodor scavenger configured to sequester a malodor molecule to reduce and/or eliminate the noxious odor the malodor molecule generates. Some embodiments can include use of a substrate configured as a non-woven fabric sheet as a delivery system for the malodor scavenger. In some embodiments, the substrate includes a polymer complexed with active ingredient to lock the active ingredient in place at a surface of the substrate via a binder so that the active ingredient is present at a predetermined activity level. After interacting with malodor molecules, at least some of the active ingredient can migrate via passive diffusion to the substrate surface to maintain the predetermined activity level.

7 Claims, 9 Drawing Sheets

NON-WOVEN FABRIC SHEET

CROSS-REFERENCE TO RELATED APPLICATIONS

This utility patent application is a continuation application of U.S. application Ser. No. 16/240,023 filed on Jan. 4, 2019, which is a continuation-in-part application of U.S. utility application Ser. No. 16/020,075 filed on Jun. 27, 2018, which is related to and claims the benefit of U.S. Provisional Application No. 62/635,324 filed on Feb. 26, 2018 and co-pending U.S. Design application No. 29/631,240 filed on Dec. 28, 2017, each of which is incorporated herein by reference in its entirety.

FIELD OF THE INVENTION

The present invention relates to a malodor control system that can include use of a malodor scavenger configured to sequester a malodor molecule to reduce and/or eliminate the noxious odor the malodor molecule generates.

BACKGROUND OF THE INVENTION

Known methods and systems for counteracting malodors can involve use of high levels of fragrance to simply "drown out" or "mask" the malodor in question. This approach could result in an unacceptably high fragrance intensity and inefficient use of materials. Known methods and systems can be appreciated from U.S. Pat. Nos. 9,233,516 and 9,795,142.

SUMMARY OF THE INVENTION

Embodiments can include a malodor control system. The malodor control system can include a substrate containing a malodor scavenger. The malodor scavenger can include at least one active ingredient configured to form a chemical complex upon contact with at least one target atom/molecule of a malodor molecule. In some embodiments, the malodor molecule activates at least one olfactory receptor of a human. In some embodiments, the chemical complex can be configured to not activate the at least one olfactory receptor of the human.

In some embodiments, the substrate can be at least one of a liquid, a solid, and a gel. In some embodiments, the malodor scavenger can be capable of being formulated into at least one of a solution and a compound. In some embodiments, the formulated solution and/or compound can be used as product in a delivery system comprising at least one of a spray dispensing system, an aerosol dispensing system, wet wipe system, and a gel or dry solid dispersion or diffusion system. In some embodiments, the malodor molecule can include at least one of hydrogen sulfide, dimethyl sulfide, methanethiol, ethanethiol, putrescine and cadaverine, indole and skatole, dimethyl trisulfide, 2,3-dimethyl-5-methyl pyrazine, trimethylamine, and ammonia.

In some embodiments, the at least one target atom/molecule can include at least one of a sulfur atom, a sulfurous molecule, a nitrogen atom, and a nitrogenous molecule. In some embodiments, the at least one active ingredient can include silver. In some embodiments, the silver can be in a form of colloidal silver, metal silver, silver particles, micro-silver, nano-silver, and/or silver containing molecules/compounds. In some embodiments, the at least one active ingredient can include silver nitrate.

Embodiments can include a delivery system for malodor control. The delivery system can include a non-woven sheet containing a malodor scavenger. The malodor scavenger can include at least one active ingredient configured to form a chemical complex upon contact with at least one target atom/molecule of a malodor molecule. The malodor molecule activates at least one olfactory receptor of a human. The chemical complex can be configured to not activate the at least one olfactory receptor of the human. The malodor scavenger can be configured to remain on the non-woven sheet until the malodor molecule makes contact with the malodor scavenger.

In some embodiments, the non-woven sheet can include a blend of polyester and rayon. In some embodiments, the blend of polyester and rayon can be a ratio of 90% polyester-10% rayon. In some embodiments, the non-woven sheet can have a weight density within a range from 1.3 ounces per square yard ($oz/yd^2$) to 4.5 $oz/yd^2$. Some embodiments can include a plurality of non-woven sheets. In some embodiments, each individual non-woven sheet of the plurality of non-woven sheets can include an adhesive applied to a portion thereof. In some embodiments, the plurality of non-woven sheets can be stacked to form a tablet. In some embodiments, the plurality of non-woven sheets can be packaged in a container.

Embodiments can include a method for malodor control. The method can involve placing a substrate containing a malodor scavenger in, or proximal to, an environment containing at least one malodor molecule. The malodor scavenger can include at least one active ingredient configured to form a chemical complex upon contact with at least one target atom/molecule of the at least one malodor molecule. The at least one malodor molecule activates at least one olfactory receptor of a human. The chemical complex can be configured to not activate the at least one olfactory receptor of the human. The method can involve allowing the at least one malodor molecule to make contact with the malodor scavenger, causing the at least one active ingredient to bond to the at least one target atom/molecule to form the chemical complex.

In some embodiments, the bond of the at least one active ingredient to the at least one target atom/molecule can be via an irreversible stoichiometric process. In some embodiments, placing the substrate in, or proximal to, the environment can involve placing the substrate at or near a malodor source generating the at least one malodor molecule. In some embodiments, placing the substrate at or near the malodor source can involve adhering the substrate to a surface of a structure.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other objects, aspects, features, advantages and possible applications of the present innovation will be more apparent from the following more particular description thereof, presented in conjunction with the following drawings. Like reference numbers used in the drawings may identify like components.

DETAILED DESCRIPTION OF THE INVENTION

The following description is of exemplary embodiments that are presently contemplated for carrying out the present invention. This description is not to be taken in a limiting sense, but is made merely for the purpose of describing the general principles and features of the present invention. The scope of the present invention is not limited by this description.

Figure 1:
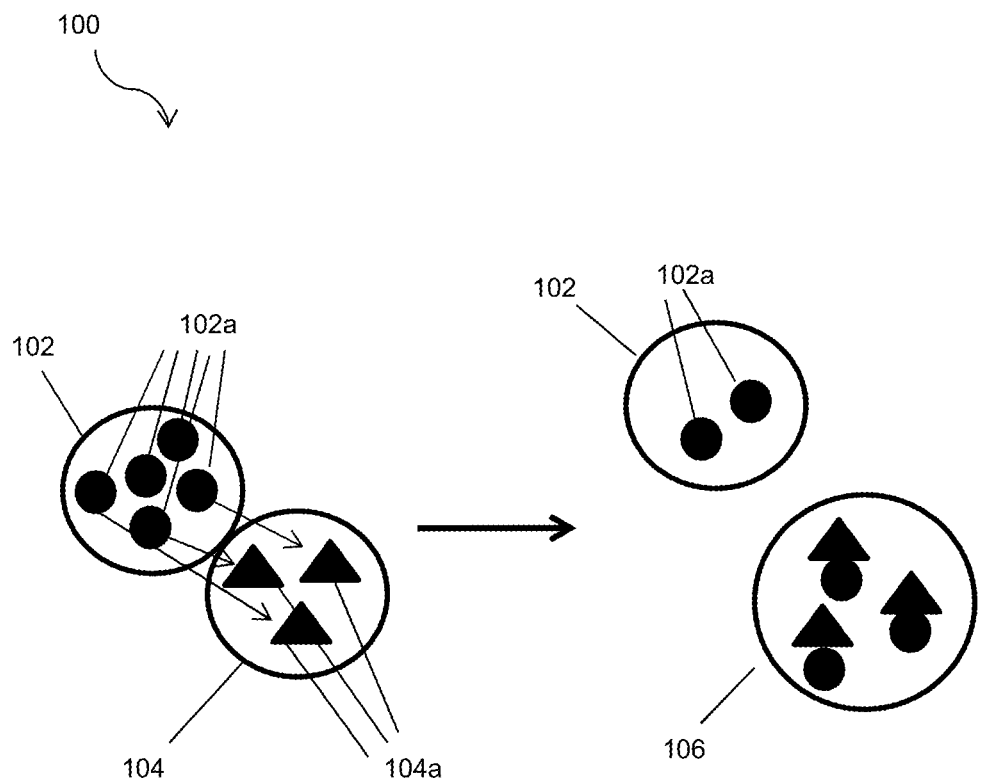
FIG. 1 is an exemplary embodiment of the malodor control system showing a malodor scavenger sequestering a malodor molecule.
Figure 2:
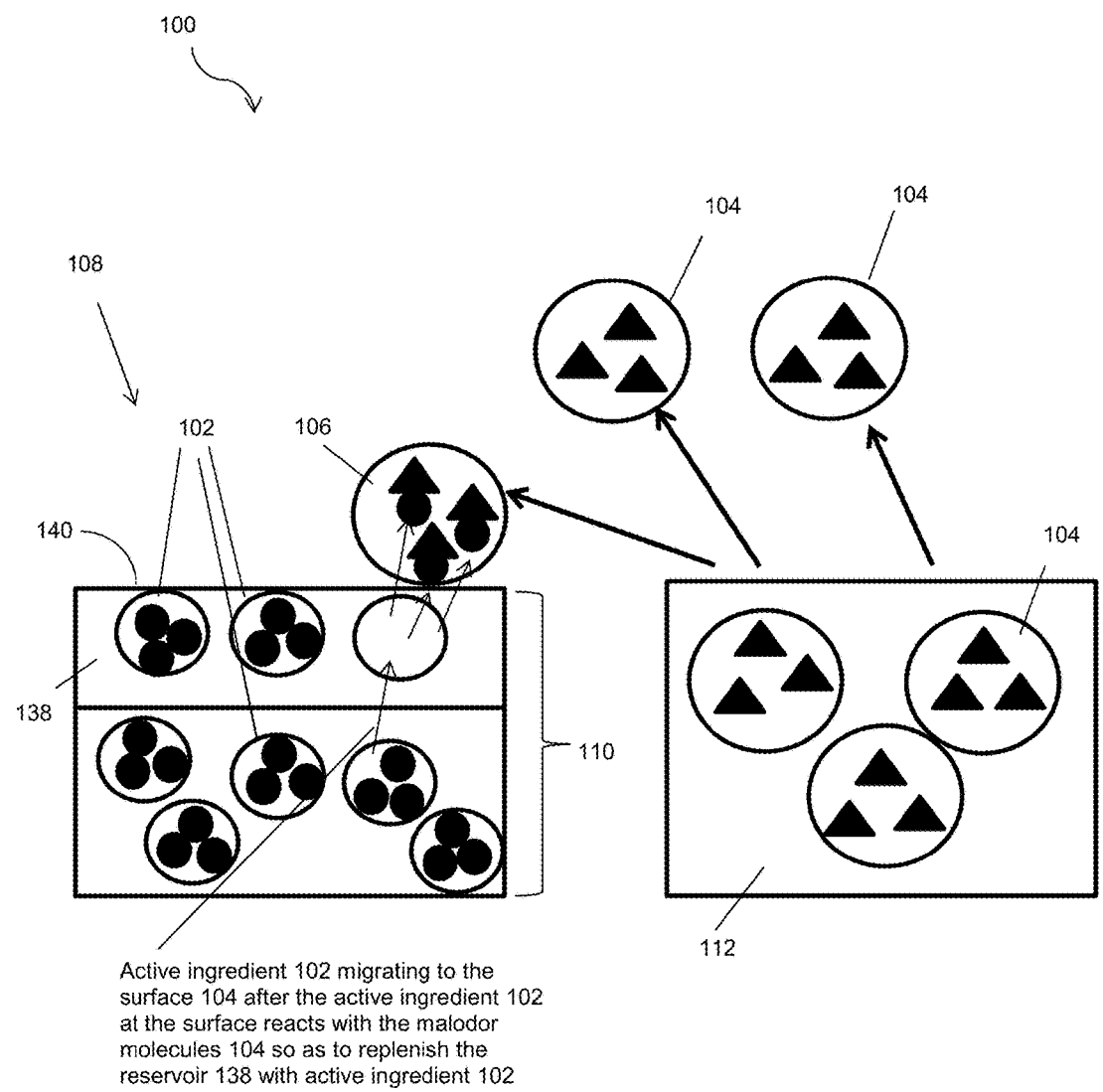
FIG. 2 is an exemplary delivery system that may be used with an embodiment of the malodor control system.

Referring to FIGS. 1-2, embodiments can relate to a malodor control system 100. Embodiments of the malodor control system 100 can include a malodor scavenger 102 configured to sequester a malodor molecule 104 to reduce and/or eliminate the noxious odor the malodor molecule 104 generates. In some embodiments, the sequestering can include the malodor scavenger 102 bonding with the malodor molecule 104 to form a chemical complex 106. The chemical complex 106 can be perceived (by a human) as odorless. For instance, the chemical complex 106 can exhibit a molecular shape or some other chemical characteristic that does not activate olfactory receptors of a human (or at least prevents or inhibits the malodor molecule 104 from activating olfactory receptors of a human), thereby neutralizing the odor of the malodor molecule 104. In some embodiments, the chemical complex 106 can be configured to activate certain olfactory receptors but not others, thereby generating a pleasant smell to a human. The bonding can include the malodor scavenger 102 latching onto the malodor molecule 104 when it comes into contact with the malodor molecule 104 via an irreversible stoichiometric process. The irreversible stoichiometric process can include the malodor scavenger 102 permanently bonding with the malodor molecule 104 on a molecular level.

Malodor molecules 104 typically associated with human waste, pet odor, and bacterial decomposition of organic matter include, but are not limited to, the following: hydrogen sulfide (rotten eggs), dimethyl sulfide & methanethiol (rotten cabbage), ethanethiol (natural gas), putrescine & cadaverine (rotting meat), indole & skatole (skunk), dimethyl trisulfide (sulfurous), 2,3-dimethyl-5-methyl pyrazine (earthy), trimethylamine (fishy) and ammonia (pungent medicinal). Embodiments of the malodor scavenger 102 can be configured to permanently bond with any one or combination of these compounds on a molecular level. This can be done to render these malodor molecules 104 odorless.

As the common malodor molecules 104 (e.g., malodor molecules 104 commonly experiences by humans) contain some form of sulfur and/or nitrogen, the malodor scavenger 102 can be configured to sequester sulfur atoms (or sulfurous molecules) and/or nitrogen atoms (or nitrogenous molecules) found in the malodor molecules 104. Furthermore, the malodor molecules 104 including sulfur atoms (or sulfurous molecules) and/or nitrogen atoms (or nitrogenous molecules) tend to be very potent (e.g., a microscopic amount of these malodor molecules 104 tend to have a major impact on ambient odor), and thus neutralizing these malodor molecules 104 can significantly improve the ambient odor. While exemplary embodiments of the malodor control system 100 describe and illustrate a malodor scavenger 102 configured to sequester sulfur atoms and/or nitrogen atoms, it is understood that the malodor scavenger 102 can be configured to sequester other target atoms/molecules 104*a* of the same type of malodor molecules 104 or other types of malodor molecules 104.

It is contemplated for the malodor scavenger 102 to include at least one active ingredient 102*a*. The active ingredient 102*a* can be a charged particle having a large surface area that allows it to latch onto the target atoms/molecules 104*a* of the malodor molecule 104. Other factors in selecting an active ingredient 102*a* can include reaction kinetics (e.g., generally the faster the active ingredient 102*a* can react with the target atoms/molecules 104*a* the better), chemical stability of the active ingredient 102*a*, the active ingredient 102*a* being non-hazardous, the ability of the active ingredient 102*a* to be controllably released from its delivery system 108, the efficacy of the active ingredient 102*a* within a wide range of use levels (e.g., being effective in sequestering target atoms/molecules form a wide range of malodor molecules), the ability of the active ingredient 102*a* to be non-reactive with a substrate that may be used as a carrier for the active ingredient 102*a*, the ability of the active ingredient 102*a* to be thermally stable, the ability of the active ingredient 102*a* to be formulated with other products, etc.

In some embodiments, the malodor scavenger 102 can include silver as the active ingredient 102*a*. The silver active ingredient can take the form of colloidal silver, metal silver, silver particles, micro-silver, nano-silver, and/or silver containing molecules/compounds. In at least one embodiment, the silver active ingredient can be silver nitrate. Silver nitrate can be an effective scavenger for target atoms/molecules 104*a* that include sulfur atoms (or sulfurous molecules) and/or nitrogen atoms (or nitrogenous molecules). For example, silver nitrate can be an effective scavenger in an activity level range from 15 parts per million (ppm) to 1500 ppm (the amount of silver nitrate adhered to the nonwoven substrate). Effectiveness of a scavenger can be defined as a complete elimination of the malodor. Generally, the faster the elimination occurs, the better. Test results reveal that malodor is eliminated by using an embodiment of the malodor control system 100 in less than 1 minute in an enclosed chamber. The quantity of active ingredient will determine the rate at which the malodor will be sequestered and for how long. In addition, silver nitrate has a neutral pH, has low viscosity in solution, is visually clear, extremely stable, and is registered by the U.S. Environmental Protection Agency as an antimicrobial.

As noted above, the bonding can include the malodor scavenger 102 latching onto the malodor molecule 104 when it comes into contact with the malodor molecule 104 via an irreversible stoichiometric process. With silver as the active ingredient 102*a*, a non-limiting example of an irreversible stoichiometric process can include silver nitrate (AgNO$_3$)+ hydrogen sulfide (H$_2$S)→silver sulfide (Ag$_2$S)+nitric acid (2HNO$_3$). Hydrogen sulfide would be rotten egg smell and silver sulfide would be odorless. With silver as the active ingredient 102a, silver nitrate can release silver such that the silver complexes with sulfur via an ionic bond formation:

2Ag+H$_2$S→Ag$_2$S+_H$_2$.

Other active ingredients 102a can be used. These can include zinc compounds. For example, zinc compounds, such as zinc ricinoleate, can bind to sulfur, nitrogen, and/or short chain fatty acids to reduce malodor.

In some embodiments, the active ingredient 102a is the malodor scavenger 102. In some embodiments, the active ingredient 102a can be formulated with other ingredients (which may include other active ingredients 102a) to generate a compound or a solution. The resulting compound or solution can be the malodor scavenger 102.

Embodiments of the malodor control system 100 can include a delivery system 108. The delivery system 108 can include the malodor scavenger 102 formulated as a compound or solution. The compound or solution can be a liquid, a spray (e.g., mixture of silver nitrate in water), a gel (e.g., carrageenan gel with the addition of silver nitrate), or a solid (e.g., sintered plastic with silver nitrate absorbed onto the surface) from which the active ingredient 102a is exposed to an environment containing malodor molecules 104 and/or is exposed to the malodor molecules 104. For example, the delivery system 108 can be a spray dispensing system (e.g., spray pump) or an aerosol dispensing system (e.g., aerosol bottle or can) containing a malodor scavenger solution or compound that can release the malodor scavenger 102 into an environment containing malodor molecules 104. As another example, the delivery system 108 can be a wet wipe system, wherein each wet wipe contains a malodor scavenger solution and/or compound that can expose the malodor scavenger 102 to malodor molecules 104 when the wet wipe is used to clean a surface containing the malodor molecules 104. As another example, the delivery system 108 can be a gel or dry solid dispersion or diffusion system (e.g., cleaning product, soap, air freshener, etc.), wherein the gel or dry solid contains a malodor scavenger solution or compound that can release the malodor scavenger 102 into an environment containing malodor molecules 104 and/or expose the malodor scavenger 102 to malodor molecules 104.

While spray, pump, and aerosol type delivery systems 108 can be an efficient means to introduce the malodor scavenger 102 to an environment, the efficacy of the malodor scavenger 102 is based on the direct contact the active ingredient 102a makes with the malodor molecule 104, the rate with which the active ingredient 102a bonds with the malodor molecules 104, and the amount of the malodor molecules 104 that becomes neutralized. One of the ways to improve the efficacy can be via the delivery system 108. The efficacy can be measured via a smell test.

In at least one embodiment, the delivery system 108 can include a means to allow the malodor molecules 104 to come into contact with the malodor scavenger 102. The delivery system 108 can include a substrate 110 containing the malodor scavenger 102. The substrate 110 can be a solid substrate 110. The substrate 110 can be configured to not react with the active ingredient 102a. The substrate 110 can be placed at or near a malodor source 112 (e.g., a source generating the malodor molecules 104). A malodor source 112 can garbage, feces, etc., and thus placing the substrate 110 at or near the malodor source 112 can include placing the substrate 110 on a garbage can, a litter box, etc.

Figure 3:
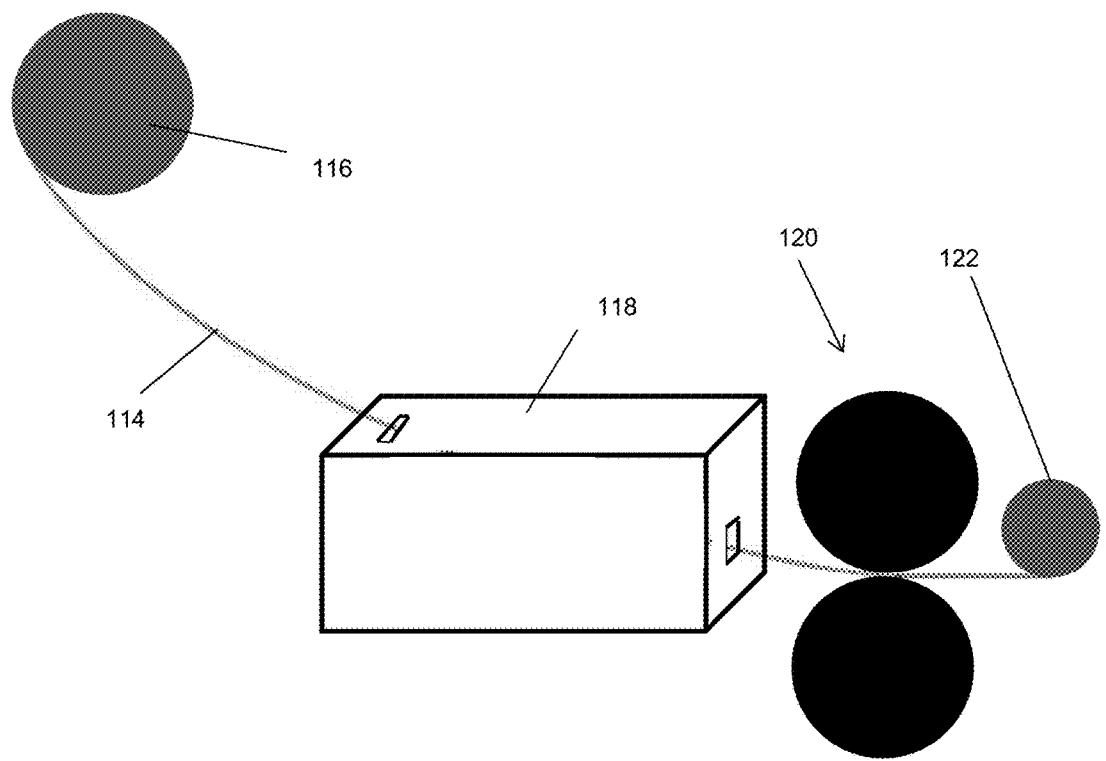
FIG. 3 shows an exemplary embodiment of a system to apply a malodor scavenger solution to an embodiment of a substrate.

Referring to FIG. 3, in at least one embodiment, the substrate 110 can be in a form of a sheet 114. The sheet 114 can be a fabric sheet. The sheet 114 can be a non-woven fabric sheet (e.g., fabric-like material that is bonded together without being woven or knitted). At least a portion of the sheet 114 can be treated with the malodor scavenger 102. This can include applying a solution or a compound of the malodor scavenger 102 to a surface of the sheet 114, impregnating a portion of the sheet 114 with a solution or a compound of the malodor scavenger 102, etc. For example, the substrate 110 can be a non-woven fabric sheet configured to be a carrier for the malodor scavenger 102.

In at least one embodiment, the non-woven fabric sheet 114 can be a blend of polyester and rayon. Generally, the higher the rayon content, the greater the amount of polar liquid the non-woven fabric sheet 114 will hold. This can increase the amount of active ingredient 102a that is held by the sheet 114. The blend can be a thermally or chemically bonded blend of polyester and rayon. The blend can be 95% polyester-5% rayon ratio, 90% polyester-10% rayon ratio, 85% polyester-15% rayon ratio, 80% polyester-20% rayon ratio, 75% polyester-25% rayon ratio, 70% polyester-30% rayon ratio, 65% polyester-35% rayon ratio, 60% polyester-40% rayon ratio, 55% polyester-45% rayon ratio, 50% polyester-50% rayon ratio, 45% polyester-55% rayon ratio, 40% polyester-60% rayon ratio, 35% polyester-65% rayon ratio, 30% polyester-70% rayon ratio, 25% polyester-75% rayon ratio, 20% polyester-80% rayon ratio, 15% polyester-85% rayon ratio, 10% polyester-90% rayon ratio, or 5% polyester-95% rayon ratio.

Embodiments of the non-woven fabric sheet 114 can be made by feeding raw polyester fibers and rayon fibers are into a series of rollers, wherein liquid is added to make a uniform slurry. The fiber mix can be rolled again, heated, and dried to form a nonwoven film.

In at least one embodiment, a non-woven fabric sheet 114 fabricated from a 90% polyester-10% rayon ratio blend can include silver nitrate active ingredient 102a residual with an activity level in excess of 1500 ppm.

The substrate formed as a sheet 114 have a weight density within a range from 1.3 ounces per square yard (oz/yd$^2$) to 4.5 oz/yd$^2$. Thus, a sheet 114 can be configured as a flat sheet (e.g., at or near 1.3 oz/yd$^2$) to a fluffed sheet 114 (e.g., at or near 4.5 oz/yd$^2$). Generally, the flatter the sheet 114, the higher the activity level can be achieved. The activity level can be defined as the amount of active ingredient 102a that is deposited on the sheet 114.

In at least one embodiment, the substrate formed as a sheet 114 can be wound about a first spool 116 as it is formed. The sheet 114 can be drawn from the first spool 116 and directed through a trough 118. The trough 118 can have a solution containing a malodor scavenger 102. As the sheet 114 is directed through the trough 118, at least a portion of the sheet 114 can come into contact with the malodor scavenger 102. At least some of the malodor scavenger 102 that comes into contact with the portion of the sheet 114 can adhere to or impregnate at least a portion of the sheet 114. This can include adhering to or impregnating at least a surface of the sheet 114. In some embodiments, the sheet 114 exiting the through 118 can be directed trough at least one roller assembly 120 to remove excess malodor scavenger solution, the excess malodor scavenger solution being the malodor scavenger solution that has not adhered to or impregnated the sheet 114. For example, the roller assembly 120 can include two rollers positioned adjacent each other so as to draw the sheet 114 between the two and exert pressure on the sheet 114 to cause the excess malodor scavenger solution to be expelled from the sheet 114. In some embodiments, the sheet 114, after the malodor scavenger solution has adhered to or impregnated a portion of the sheet 114, can be dried. This can include exposing the sheet 114, or a portion of the sheet 114 having the malodor scavenger solution applied thereto, to hot air. In some embodiments, the sheet 114 having the malodor scavenger solution applied thereto can be wound about a second spool 122.

Figure 4:
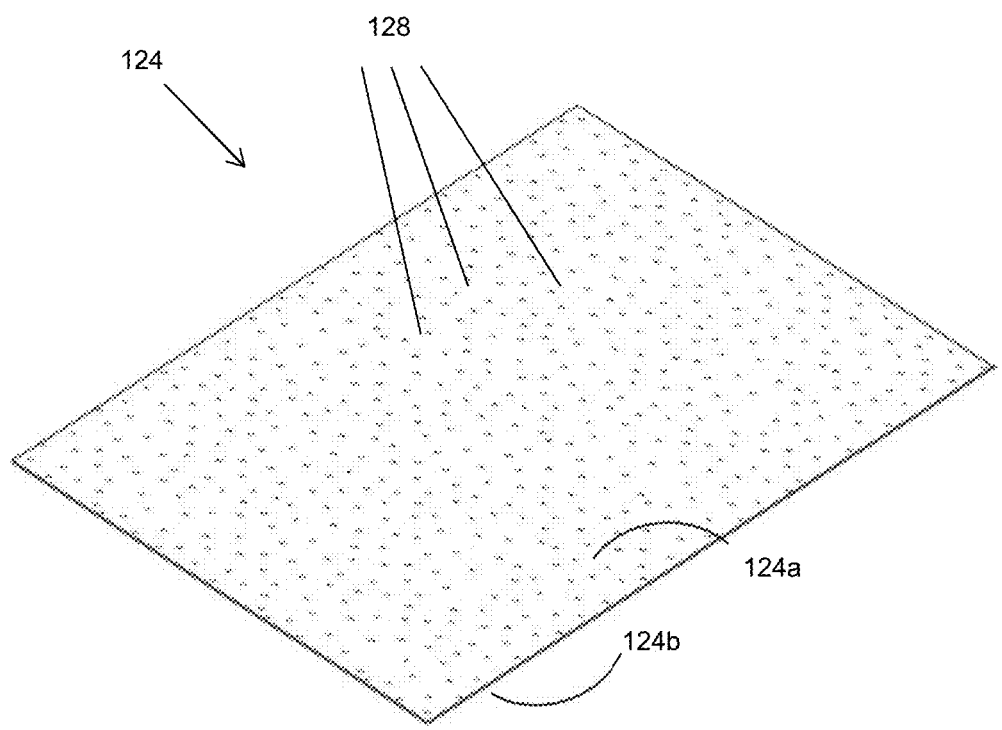
FIG. 4 shows an embodiment of a substrate configured as an individual sheet.

Referring to FIG. 4, in some embodiments, the sheet 114 having the malodor scavenger solution applied thereto can undergo further processing. The further processing can include generating individual sheets 124. The individual sheets 124 can be portions of the sheet 114 having the malodor scavenger solution applied thereto. For example, an individual sheet 124 can be a section of the sheet 114 having the malodor scavenger solution applied thereto that has been generated by cutting individual sheets 124 form the sheet 114. The individual sheet 124 can be a square or rectangular sheet have a first surface 124*a*, a second surface 124*b*, a length 124*c* (ranging from 1 inch to 40 inches), a width 124*d* (ranging from 1 inch to 40 inches), a thickness 124*e* (ranging from ¹⁄₃₂ of an inch to ⅛ of an inch), a sheet top 124*f*, a sheet bottom 124*g*, a first sheet side 124*h*, and a second sheet side 124*i*. The individual sheet 124 can be in a shape other than a square or rectangle, which can be a circular shape, a hexagonal shape, etc. The individual sheet 124 can have the malodor scavenger solution applied to any portion of the first surface 124*a* and/or the second surface 124*b* to generate a treated surface area 128 of the individual sheet 124.

It is contemplated for some individual sheets 124 to have a length 124*c* of 10 feet and a width 124*d* of 20 feet. This may be done to make tarp-sized sheets 124 that can be used as odor absorbing tarps for industrial applications. For example, odor absorbing tarps may be used when maintenance is being conducted on natural gas pipelines and the work crew has to expose and open a gas pipeline. While the pipeline may be shut off, there may still be residual odor in the pipeline and that can travel great distances when the workers open the pipeline for the first time. Use of the tarp can eliminate such a spread of odor.

Figure 5:
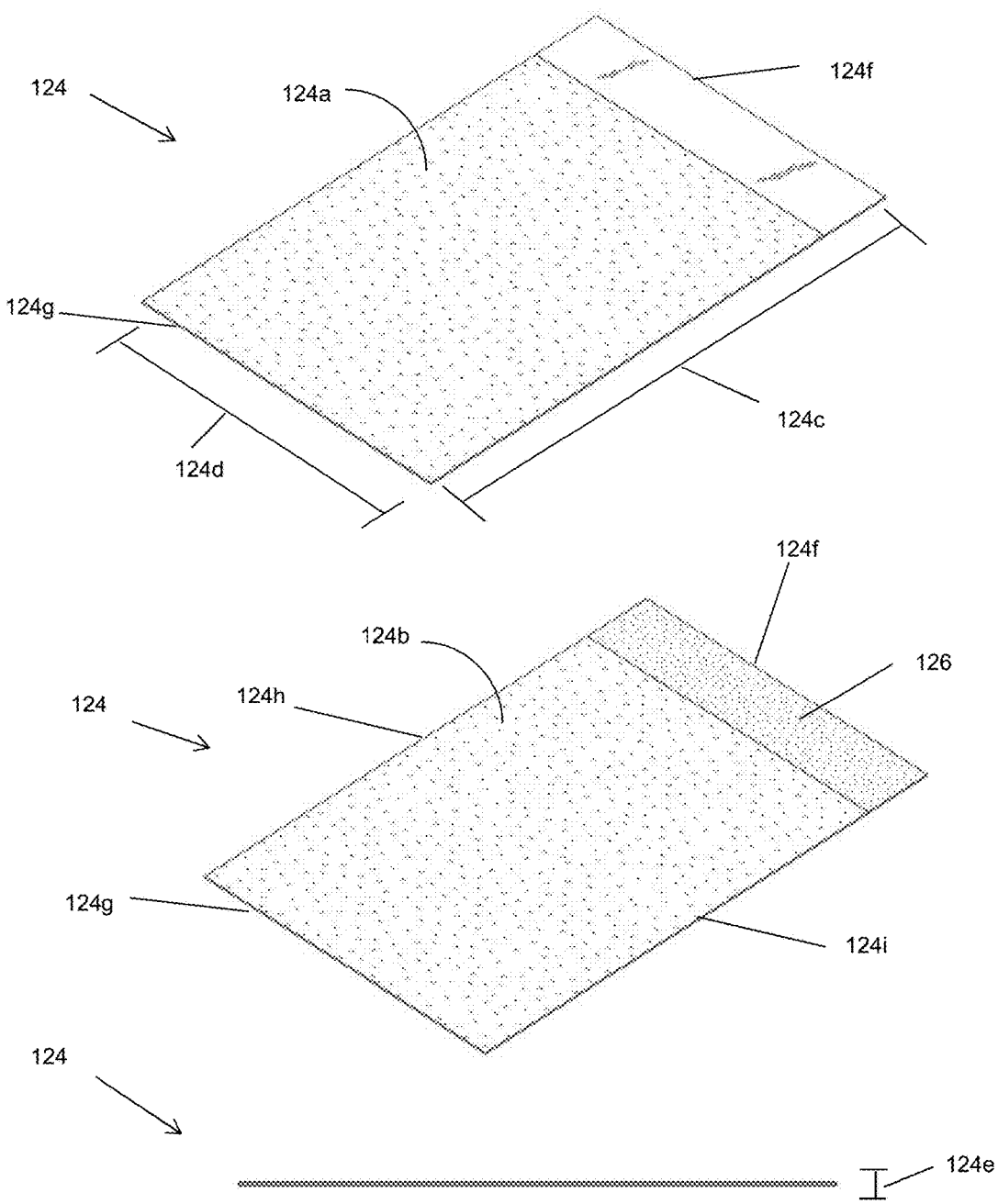
FIG. 5 shows an embodiment of a substrate configured as an individual sheet with an adhesive applied to a portion thereof.

Referring to FIG. 5, in at least one embodiment, the individual sheet 124 can have an adhesive 126 applied to a portion thereof. The adhesive 126 can facilitate temporarily attaching the individual sheet 124 to a surface of a structure (e.g., a garbage can, a litter box, etc.). In some embodiments, the adhesive 126 can be applied to the second surface 124*b*. This can allow the first surface 124*a* to be exposed to an environment that contains malodor molecules 104 by attaching the individual sheet 124 to a surface of a structure containing the malodor source 112 such that the second surface 124*b* is adjacent the structure. The individual sheet 124 can be used to cause the active ingredient 102*a* to sequester malodor molecules 104 generated from the malodor source 112. The individual sheet 124 can be used to cause the active ingredient 102*a* to sequester malodor molecules 104 generated from the malodor source 112 (thereby effectively neutralizing the malodor molecules 104) until the active ingredient 102*a* within the individual sheet 124 is consumed. For example, an individual sheet 124 having a treated surface area 128 (a surface area containing a malodor scavenger solution with a silver nitrate active ingredient) of 20-40 square inches can be used to sequester sulfur atoms (or sulfurous molecules) and/or nitrogen atoms (or nitrogenous molecules) from a malodor source 112 (thereby effectively neutralizing the sulfur atoms (or sulfurous molecules) and/or nitrogen atoms (or nitrogenous molecules) for a time period within the range from 24 hours (1 day) to 336 hours (14 days), depending on the concentration of the malodor molecules 104 and the rate at which the malodor molecules 104 are being generated.

Figure 6:
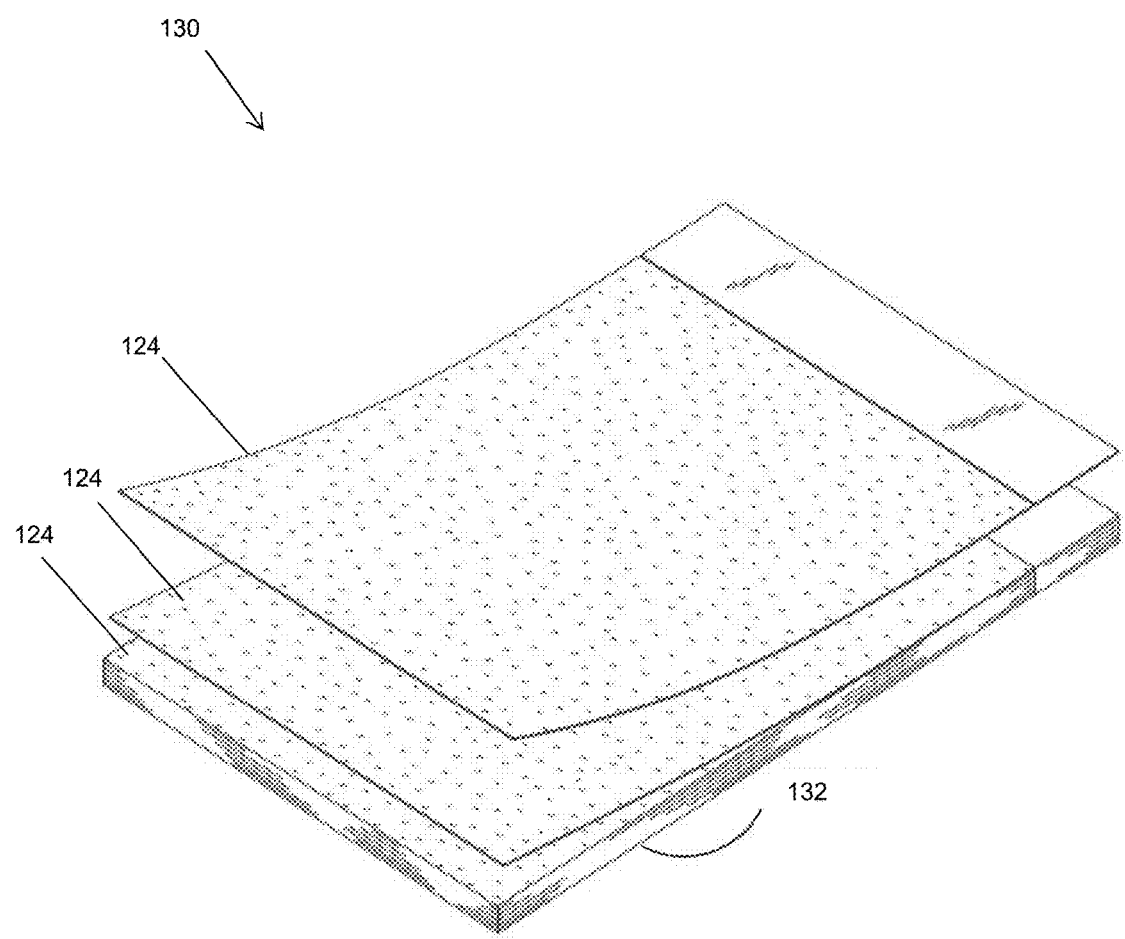
FIG. 6 shows an embodiment of a tablet that can be used to contain and distribute a stack of individual sheets.

Referring to FIG. 6, in some embodiments, a plurality of individual sheets 124 can be stacked to form a tablet 130. For example, the adhesive 126 can be applied to the second surface 124*b* of each individual sheet 124 at a sheet top 124*f*. A first individual sheet 124 in the stack can be placed on top of a tablet backing 132. The tablet backing 132 can be a piece of cardboard, for example. The first individual sheet 124 can be placed on top of the tablet backing 132 such that the second surface 124*b* of the first individual sheet 124 is adjacent the tablet backing 132. This can cause the adhesive 126 of the first individual sheet 124 to temporarily hold the first individual sheet 124 in place against the tablet backing 132 until the first individual sheet 124 is removed by pulling the first individual sheet 124 from the tablet backing 132. A second individual sheet 124 in the stack can be placed on top of a first individual sheet 124. The second individual sheet 124 can be placed on top of the first individual sheet 124 such that the second surface 124*b* of the second individual sheet 124 is adjacent the first surface 124*a* of the first individual sheet 124. This can cause the adhesive 126 of the second individual sheet 124 to temporarily hold the second individual sheet 124 in place against the first surface 124*a* of the first individual sheet 124 until the second individual sheet 124 is removed by pulling the second individual sheet 124 from the first individual sheet 124. Additional individual sheets 124 (e.g., a third individual sheet 124, a fourth individual sheet 124, a fifth individual sheet 124, etc.) can be added to the stack in a similar fashion. In use, an individual sheet 124 can be removed from the stack and adhered to a surface of a structure (e.g., a garbage can, a litter box, etc.), as described above.

Figure 7:
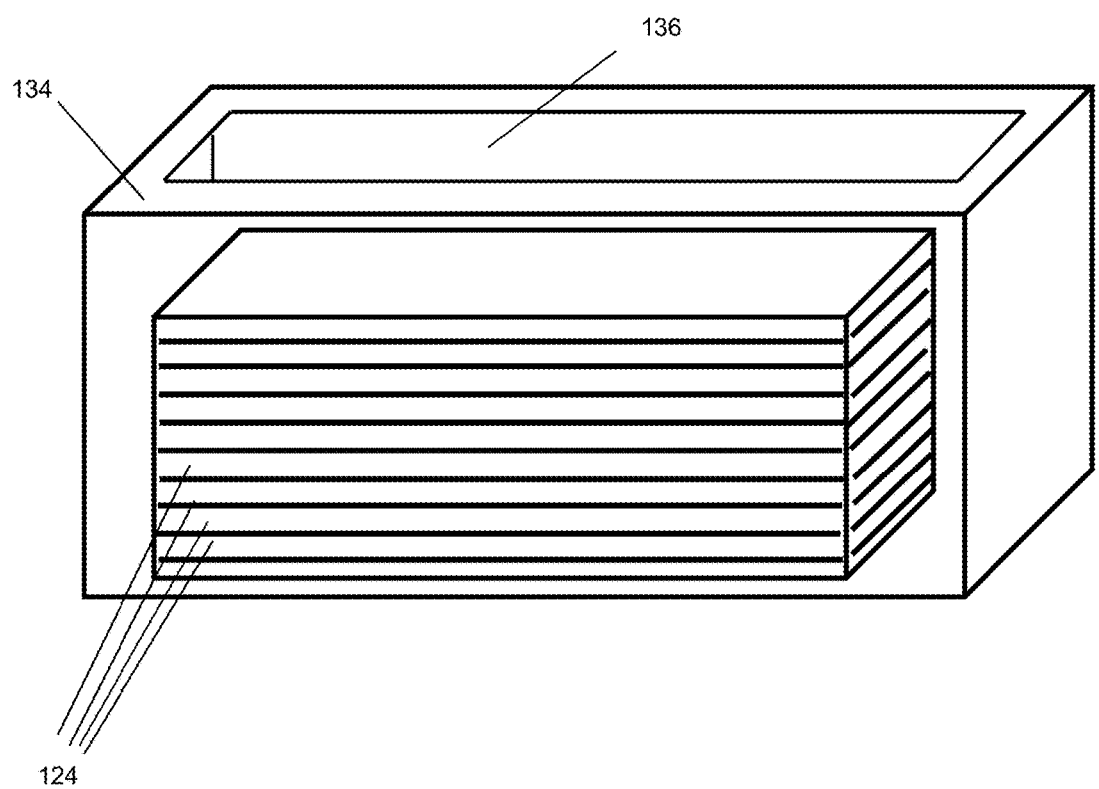
FIG. 7 shows an embodiment of a container that can be used to contain and distribute a stack of individual sheets.

Referring to FIG. 7, in some embodiments, a plurality of individual sheets 124 can be packaged in a container 134. The container 134 can be a box, a pouch, etc. The individual sheets 124 can be stacked in a similar fashion as described for the tablet 130. Each individual sheet 124 can be removed from the stack by pulling the individual sheet 124 through an opening 136 in the container 134. The individual sheet 124 can then be adhered to a surface of a structure (e.g., a garbage can, a litter box, etc.), as described above.

While some embodiments describe the individual sheet 124 as having an adhesive 126 applied to a portion thereof, some embodiments do not include an adhesive 126 (see FIG. 4). For example, the individual sheets 124 can be stacked to form a tablet 130 or stacked in the container 134 without the adhesive 126 applied to the second surface 124*b* of each individual sheet 124. With such embodiments, the individual sheet 124 is not adhered to a surface of a structure via the adhesive 126. Instead, the individual sheets 124 can be adhered to the structure by some other means (e.g., a clip, piece of tape, applying an adhesive to the structure or to the individual sheet just prior to using the individual sheet, etc.). Alternatively, the individual sheet 124 can be placed in proximity to the malodor source 112 without being attached to a structure.

In use, an embodiment of the substrate 110 can be placed in an environment containing at least one malodor molecule 104, placed proximal to an environment containing at least one malodor molecule 104, and/or placed in an environment expected to contain at least one malodor molecule 104. This can include placing the substrate 110 at or near a malodor source 112. As malodor molecules 104 are generated by the malodor source 112, a malodor molecule 104 can make contact with the malodor scavenger 102 of the substrate 110.

As a malodor molecule 104 makes contact with the malodor scavenger 102 of the substrate 110, at least one active ingredient 102a of the malodor scavenger 102 can bond to at least one target atom/molecule 104a of the malodor molecule 104. The bond of the active ingredient 102a to the target atom/molecule 104a can form a chemical complex 106. In some embodiments, the chemical complex 106 can remain in or on the substrate 110. In some embodiments, the active ingredient 102a can bond to the target atom/molecule 104a, forming the chemical complex 106, and be carried away (e.g., when using a spray application) with the malodor molecule 104. The chemical complex 106 can exhibit a molecular shape or some other chemical characteristic that does not activate olfactory receptors of a human (or at least prevents or inhibits the malodor molecule 104 from activating olfactory receptors of a human), thereby neutralizing the malodor molecule 104. In some embodiments, a non-volatile complex 106 can be formed that bonds to the substrate 110. In addition, the substrate 110 can be configured so that it changes color (e.g., light beige to almost black) when the active ingredient (e.g., silver nitrate) is consumed and bound to the sulfur.

The substrate 110 can be used to neutralize a plurality of malodor molecules 104 being generated by the malodor source 112. This can include neutralizing a plurality of the same type of malodor molecules 104 and/or a plurality of different types of malodor molecules 104. The substrate 110 can be used to neutralize at least some of the malodor molecules 104 being generated from the malodor source 112, which can include all of the malodor molecules 104 being generated from the malodor source 112. The substrate 110 can be used to neutralize at least some of the malodor molecules 104 being generated from the malodor source 112 until none of the active ingredient 102a is left in or on the substrate 110 to be bonded with malodor molecules 104 being generated by the malodor source 112. This can include using the substrate 110 to neutralize at least some of the malodor molecules 104 being generated from the malodor source 112 until all of the active ingredient 102a of the substrate 110 has bonded to with malodor molecules 104 to form chemical complexes 106. After the all of the active ingredient 102a of the substrate 110 has bonded to with malodor molecules 104 to form chemical complexes 106, the substrate 110 can be replaced with another substrate 110 that has malodor scavenger solution.

Figure 8:
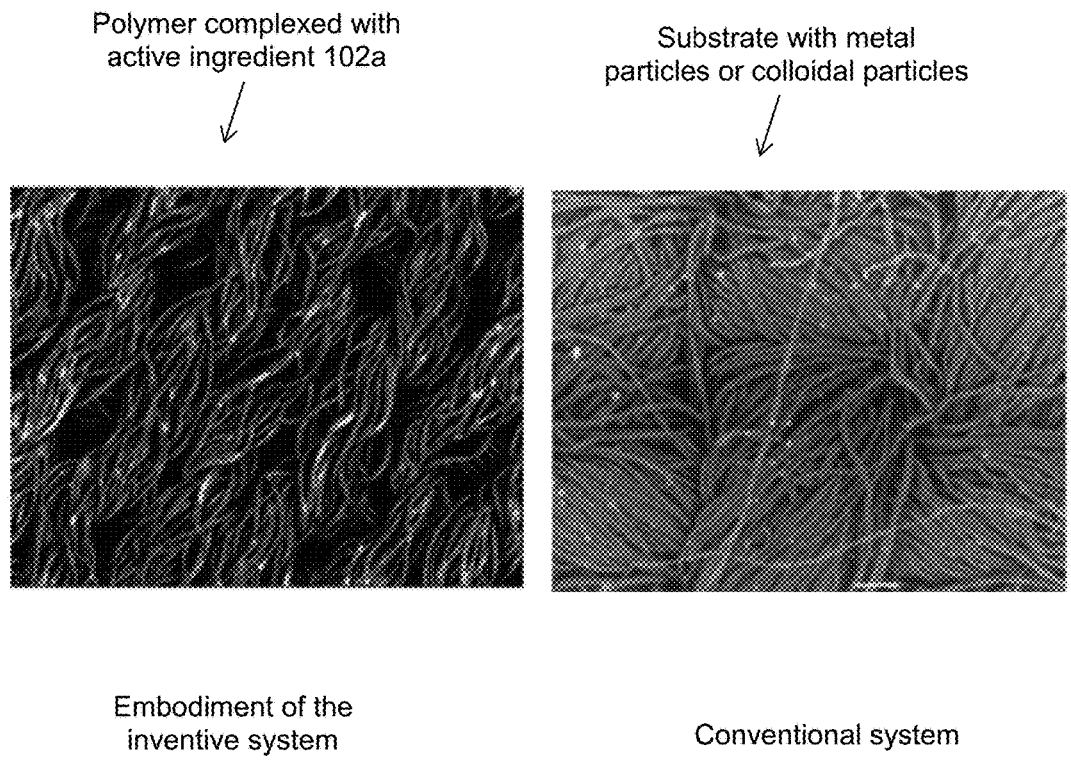
FIG. 8 illustrates an image of an embodiment of the system showing a substrate with a polymer complexed with active ingredient and an image of a conventional substrate system.
Figure 9:
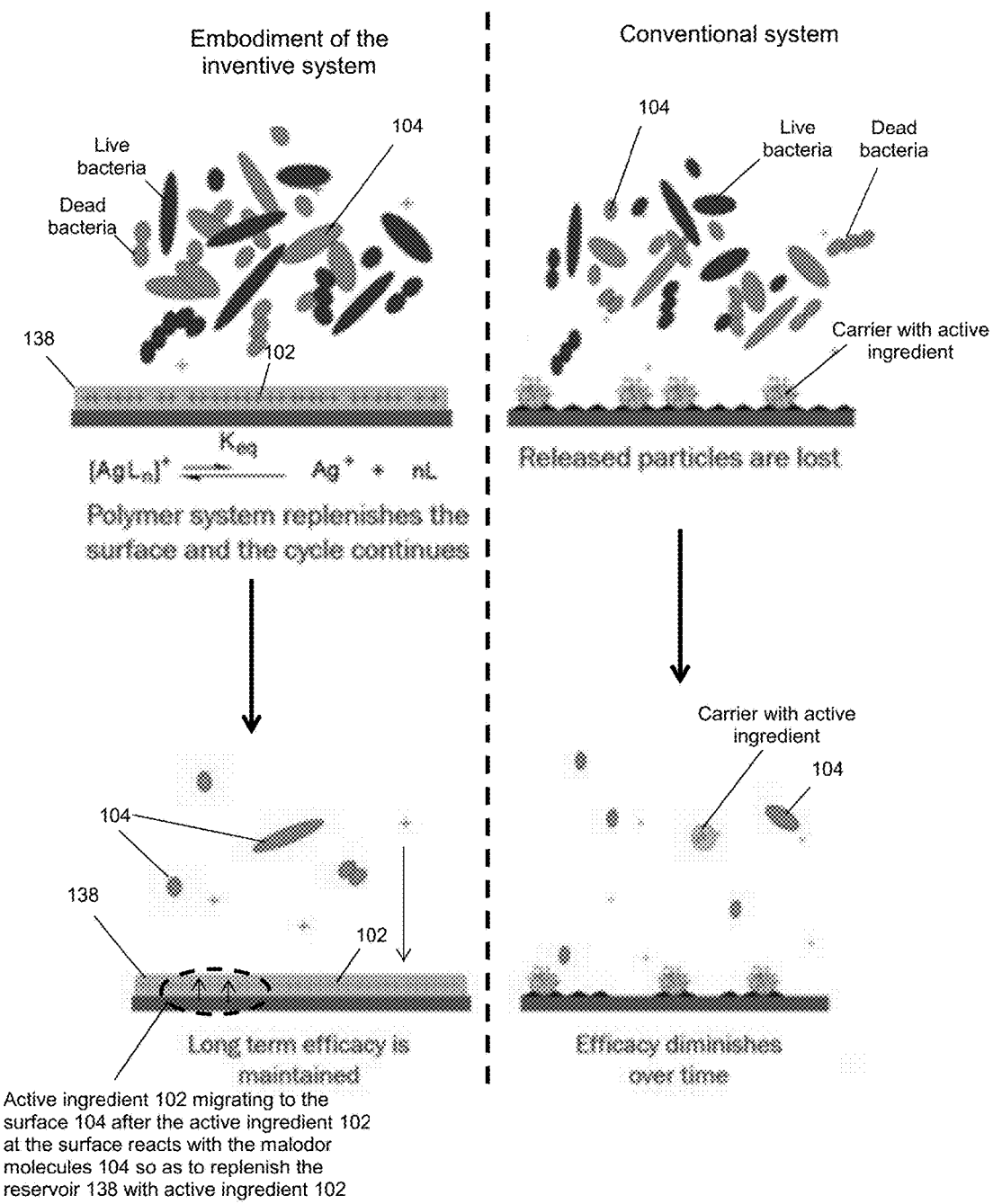
FIG. 9 shows the delivery mechanism of an embodiment of the inventive system in comparison to that of a conventional system.

Referring to FIGS. 8-9, as noted herein embodiments of the system 100 can provide a substrate 100 having an active ingredient 102a residual with an activity level in excess of 1500 ppm. This can be achieved by the binding mechanism used for malodor control by embodiments of the system 100. For instance, embodiments of the substrate 100 can include a polymer complexed with an active ingredient 102a so as to form a reservoir 138 of active ingredient 102a. The polymer complexed with active ingredient 102a, when bound to the substrate 110 (e.g., via a binder), can form a polymeric network. (See FIG. 8). As active ingredient 102a is exposed from the polymeric network to neutralize odorous compounds 104, the active ingredient 102a can be replenished at the surface 140 of the substrate 110 to maintain the odorous-neutralizing efficacy of the system 100 over time. For instance, active ingredient 102a can migrate to the surface 104 after the active ingredient 102a at the surface reacts with the malodor molecules 104 so as to replenish the reservoir 138 with active ingredient 102a. The migration can be via passive diffusion.

FIG. 9 demonstrates an exemplary delivery mechanism of an embodiment of the inventive system 100 in comparison to that of a conventional system. As can be seen from FIG. 9, the active ingredients used in conventional delivery systems are not replenished at the surface, leading to degraded efficacy over time. With the inventive system 100, the active ingredient 102a is bound to the substrate 110 via a binder working in conjunction with the polymeric network to provide consistent and prolonged exposure of active ingredient 102a at the surface 140 over a prolonged period of time. This is achieved by the binder holding the active ingredient 102a at the surface 140 and the polymeric network allowing for the migration of active ingredient 102a to the surface 140 as active ingredient 102a at the surface 140 interacts with the malodor molecules 104 so as to replenish with reservoir 138 with active ingredient and maintain a consistent and prolonged activity level at the surface 140. The migration can be via passive diffusion. This configuration can allow the system 100 to simultaneously replenish active ingredient 102a at the surface 140 to maintain a predetermined activity level for the active ingredient 102a. Thus, the system 100 can solve the technical problem plagued by conventional systems that limit conventional systems to a single use delivery scheme. For instance conventional systems deliver a single dose of active ingredient and are exhausted of any further activity, whereas the inventive system 100 exposes active ingredient 102a controllably and replenishes it within the reservoir 138 portion of the substrate 110 so that the surface 140 of the substrate 110 has a presence of active ingredient 102a at a predetermined activity level throughout the life of the system 100. Thus, the inventive system 100 provides a mechanism for malodor control that locks the active ingredient 102a in place and provides a reservoir 138 of active ingredient 102a that will be available for sustained release of active ingredients 102a when exposed to prolonged contact with odorous compounds 104.

It should be further noted that conventional systems require the use of a carrier to deliver active ingredient for malodor control. In contrast, embodiments of the inventive system 100 can supply the active ingredient 102a without the use of a carrier. For instance, conventional systems may use a carrier (e.g., $TiO_2$) that is released from a substrate so as to carry the active ingredient into the environment. The carrier then releases the active ingredient to interact with the malodor molecules 104. The inventive system 100, however, exposes the active ingredient 102a directly from the substrate 110 for interaction with the malodor molecules 104.

It should be further noted that embodiments of the substrate 110 (e.g., substrates configured to include a polymer complexed with the active ingredient 102a and the binder locking them in place) can withstand washing or liquid immersion without degrading the performance of the system 100. Common carriers are comprised of silica complexed with an active ingredient, wherein conditions of high humidity or exposure to water will dissolve the silica matrix and allow the active ingredient to be completely exposed (i.e., no controlled release) or be washed away without providing any benefit.

In an exemplary, non-limiting embodiment, the system 100 can include a substrate 110. The substrate 110 can include a binder, a polymer, and an active ingredient 102a. In some embodiments, the active ingredient 102a can be a silver nitrate solution in water to generate ionic silver. In some embodiments, the binder can be an acrylate binder. Other binders can be used, such as polyvinyl alcohol, carboxymethyl cellulose, hydroxypropylmethyl cellulose, modified starch, etc. In some embodiments, the active ingredient 102a can be a silver nitrate solution in water along with a binding system which may be an acrylate. The resulting solution is a clear homogenous liquid. This liquid can be applied to the non-woven polymeric substrate 110 at a saturated level and then rolled through a series of rollers to remove excess liquid. The wet substrate can then dried to deliver a final product with a specific activity level. Activity level is a function of intended product life and cost per unit. Activity ranges may be as low as 10 ppm to 100 ppm to 1000 ppm up to 1500 ppm, or even greater than 1500 ppm. The substrate 110 can have a surface 140 that will be exposed to a malodor molecule 104. The polymer can be complexed with the active ingredient 102a so that a predetermined amount of the active ingredient 102a is locked in place via the binder at or near the surface 140 of the substrate 110. The reservoir 138 portion can be located adjacent or just below the surface 140 of the substrate 110 so that the active ingredient 102a is present within the reservoir 138 and/or at the surface 140 at a predetermined activity level (e.g., the active ingredient 102a can be locked in place on the surface 140 of a substrate 110 to provide continuous release over an extended period of time until all the active ingredient 102a has reacted with odorous compounds 104a). The active ingredient 102a can be configured as a malodor scavenger 102 that will form a chemical complex 106 upon contact with a target atom 104a of the malodor molecule 104 and/or a target molecule 104a of the malodor molecule 104. For instance, the malodor molecule 104 can come into contact with the surface 140 of the substrate 110. The active ingredient 102a can interact with the malodor molecule 104 and/or a target molecule 104a at the surface 140 of the substrate 110 and form the chemical complex 106. After the chemical complex 106 is formed, at least some of the active ingredient 102a can migrate to the surface 140 and/or reservoir 138 portion to maintain the predetermined activity level at the reservoir 138 and/or surface 140. For instance, with reference to FIG. 9, the malodor molecules 104 can include live bacteria. After the malodor molecules 104 come in contact with the surface 140 of the substrate 110, chemical affinity can cause the active ingredient 102a to interact with the live bacteria. This interaction can cause the live bacteria to die. This can temporarily leave a void or deficiency (e.g., a temporary lower activity level) of active ingredient 102a at the surface 140. But active ingredient 102a can migrate from the reservoir 138 to the surface 140 to replenish that void or deficiency. Similarly, active ingredient 102a can migrate from other portions of the substrate 110 to replenish active ingredient 102a at the reservoir 138. The migration can be via passive diffusion. In contrast, the active ingredient of conventional systems is lost after reacting with the malodor molecules 104.

In another exemplary, non-limiting embodiment, the system 100 can include a non-woven sheet 114, the non-woven sheet 114 including a binder, a polymer, and an active ingredient 102a. The non-woven sheet 114 can have a surface 140 that will be exposed to a malodor molecule 104. The polymer can be complexed with the active ingredient 102a so that a predetermined amount of the active ingredient 102a is locked in place via the binder at or near the surface 140 of the non-woven sheet 114. The reservoir 138 portion can be located adjacent or just below the surface 140 of the non-woven sheet 114 so that the active ingredient 102a is present within the reservoir 138 and/or at the surface 140 at a predetermined activity level. The active ingredient 102a can be configured as a malodor scavenger 102 that will form a chemical complex 106 upon contact with a target atom 104a of the malodor molecule 104 and/or a target molecule 104a of the malodor molecule 104. For instance, the mal-odor molecule 104 can come into contact with the surface 140 of the non-woven sheet 114. The active ingredient 102a can interact with the malodor molecule 104 and/or a target molecule 104a at the surface 140 of the non-woven sheet 114 and form the chemical complex 106. After the chemical complex 106 is formed, at least some of the active ingredient 102a can migrate to surface 140 and/or the reservoir 138 portion to maintain the predetermined activity level at the reservoir 138 and/or surface 140. The migration can be via passive diffusion.

In another exemplary, non-limiting embodiment, a method for malodor control can involve placing a substrate 110 in or proximal to an environment containing a malodor molecule 104. The substrate 110 can include a binder, a polymer, and an active ingredient 102a. The polymer can be complexed with the active ingredient 102a so that a predetermined amount of the active ingredient 102a is locked in place via the binder within at or near the surface 140 of the substrate 110. The reservoir 138 portion can be located adjacent or just below the surface 140 of the substrate 110 so that the active ingredient 102a is present within the reservoir 138 and/or at the surface 140 at a predetermined activity level. The method can involve allowing the active ingredient 102a to form a chemical complex 106 upon contact with a target atom 104a of the malodor molecule 104 and/or a target molecule 104a of the malodor molecule 104. The method can involve allowing at least some of the active ingredient 102a to migrate to the surface 140 and/or to the reservoir 138 portion after the chemical complex 106 is formed to maintain the predetermined activity level at the surface 140 and/or reservoir 138. The migration can be via passive diffusion.

Benefits of the system 100 can include: 1) providing a malodor control system with improved durability (e.g., substrates can be washed (immersed in liquid) without a degradation in the odor-neutralizing capabilities of the system), improved longevity (e.g., provide a sustained release of active ingredients when exposed to prolonged contact with odorous compounds), and increased stability (e.g., heat stable) when compared to conventional systems (for instance, silver nitrate is a non-volatile active ingredient, and the combination of silver nitrate with an acrylate binder provides a system that can resist degradation at elevated temperatures (>50° C.)); 2) obviating the need for a single use delivery system, as the active ingredient 102a is attached to the substrate 110 via use of a binder working in conjunction with the polymeric network of the substrate 110; 3) obviating the need to form a colloidal or a nanoparticle with the active ingredient 102a; 3) obviating the need to use a carrier for the active ingredient 102a, as the active ingredient 102a is released from the polymer network without use of a carrier.

It should be understood that modifications to the embodiments disclosed herein can be made to meet a particular set of design criteria. For instance, the number of or configuration of substrates 110, active ingredients 102a, sheets 110, delivery systems 108, and/or other components or parameters may be used to meet a particular objective.

It will be apparent to those skilled in the art that numerous modifications and variations of the described examples and embodiments are possible in light of the above teachings of the disclosure. The disclosed examples and embodiments are presented for purposes of illustration only. Other alternative embodiments may include some or all of the features of the various embodiments disclosed herein. Therefore, it is the intent to cover all such modifications and alternative embodiments as may come within the true scope of this invention, which is to be given the full breadth thereof. Additionally, the disclosure of a range of values is a disclosure of every numerical value within that range, including the end points.

Therefore, while certain exemplary embodiments of apparatuses and methods of making and using the same have been discussed and illustrated herein, it is to be distinctly understood that the invention is not limited thereto but may be otherwise variously embodied and practiced within the scope of the following claims.

What is claimed is:

1. A delivery system for malodor control, comprising:
   a non-woven sheet comprising: a binder; a polymer; and an active ingredient;
   the non-woven sheet having a surface that will be exposed to a malodor molecule;
   the polymer being complexed with the active ingredient so that a predetermined amount of the active ingredient is locked in place via the binder at the surface and/or within a reservoir portion of the non-woven sheet so that the active ingredient is present at the surface and/or within the reservoir at a predetermined activity level;
   the active ingredient being configured as a malodor scavenger that will form a chemical complex upon contact with a target atom of the malodor molecule and/or a target molecule of the malodor molecule, wherein after the chemical complex is formed, at least some of the active ingredient migrates to the surface and/or the reservoir portion to maintain the predetermined activity level, providing a more durable, long lasting and stable system; and
   the non-woven sheet further comprising a blend of polyester and rayon.

2. The delivery system recited in claim 1, wherein the blend of polyester and rayon is a ratio ranging from 75% polyester-25% rayon through 90% polyester-10% rayon.

3. The delivery system recited in claim 1, wherein the non-woven sheet has a weight within a range from 1.3 ounces per square yard ($oz/yd^2$) to 4.5 $oz/yd^2$.

4. The delivery system recited in claim 1, further comprising a plurality of non-woven sheets stacked to form a tablet.

5. The delivery system recited in claim 4, wherein the tablet is packaged in a container.

6. A method for malodor control, comprising:
   placing a substrate in or proximal to an environment containing a malodor molecule by placing the substrate at or near a malodor source generating the malodor molecule, the substrate comprising: a binder; a polymer; and an active ingredient, the polymer being complexed with the active ingredient so that a predetermined amount of the active ingredient is locked in place via the binder at the surface and/or within a reservoir portion of the substrate so that the active ingredient is present at the surface and/or within the reservoir at a predetermined activity level;
   allowing the active ingredient to form a chemical complex upon contact with a target atom of the malodor molecule and/or a target molecule of the malodor molecule; and
   allowing at least some of the active ingredient to migrate to the surface and/or the reservoir portion after the chemical complex is formed to maintain the predetermined activity level.

7. The method recited in claim 6, wherein the chemical complex is generated via an irreversible stoichiometric process.

* * * * *